United States Patent [19]

Schreiber

[11] Patent Number: 4,635,637

[45] Date of Patent: Jan. 13, 1987

[54] SURGICAL SUTURE

[76] Inventor: Saul N. Schreiber, 6525 N. Central Ave., Phoenix, Ariz. 85012

[21] Appl. No.: 595,330

[22] Filed: Mar. 29, 1984

[51] Int. Cl.⁴ .......................................... A61B 17/04
[52] U.S. Cl. .................................... 128/337; 128/335
[58] Field of Search ............... 128/337, 92 B, 92 BA, 128/334 R, 334 C, 335, 335.5; 411/339, 446, 450, 451, 457, 458, 456

[56] References Cited

U.S. PATENT DOCUMENTS

| | | | |
|---|---|---|---|
| 1,206,425 | 11/1916 | Feasey | 411/456 |
| 1,311,903 | 8/1919 | Leschandler | 411/456 |
| 3,236,142 | 2/1966 | Bradway | 411/457 |
| 3,716,058 | 2/1973 | Tanner, Jr. | 128/337 |
| 3,757,629 | 9/1973 | Schneider | 411/457 |
| 4,263,903 | 4/1981 | Griggs | 128/337 |
| 4,454,875 | 6/1984 | Pratt et al. | 128/92 B |

OTHER PUBLICATIONS

"Brickham's Operative Surgery", 1924, p. 368.

Primary Examiner—Richard C. Pinkham
Assistant Examiner—T. Brown
Attorney, Agent, or Firm—Weiss & Associates

[57] ABSTRACT

A surgical suture and a delivery system for positioning and inserting the suture is disclosed. The suture includes a base member having two substantially parallel, rigid, barbed shafts upstanding therefrom. The delivery system includes a hollow sleeve member having an elongate cross section with the long dimension of the cross section sufficient to accommodate the width of the base member. In use, the end of the hollow sleeve is positioned adjacent a body tissue wound which is to be repaired and the suture is inserted into the tissue by pushing the suture through the sleeve by means of a pusher member. If necessary, a starter member is first pushed through the sleeve to provide started openings in the tissue into which the barbed shafts are then inserted.

4 Claims, 6 Drawing Figures

SURGICAL SUTURE

BACKGROUND OF THE INVENTION

This invention relates generally to surgical sutures and to suturing systems, and more specifically to a surgical suture and system for repairing meniscus tissue. This invention is an improvement on the sutures disclosed and claimed in my copending application, entitled, "Surgical Fasteners and Method," filed Feb. 28, 1984, the disclosure of which is incorporated herein by reference.

There are a number of techniques used for closing and repairing incisions, tears, or wounds in body tissue. These include, for example, the use of stitches, staples, tape, clamps, the sutures disclosed in my above-identified copending aplication, and the like. The technique used in a particular application depends on the size, nature, location of the opening or tear, and the like. Despite the wide range of available techniques, however, a need still existed for a surgical suture which would provide the ease and precision of insertion in arthroscopic surgery of my previously disclosed suture, but which would provide an even more secure joining of the body tissue, especially meniscus tissue.

It is therefore an object of this invention to provide an improved surgical suture.

It is further object of this invention to provide an improved surgical suture and system for placement and insertion of the suture.

It is another object of this invention to provide an improved suture for arthroscopic surgery.

BRIEF SUMMARY OF THE INVENTION

The foregoing and other objects and advantages of the invention are achieved with the multiple shafted suture and system as herein described. In one embodiment of the invention, the suture includes a base member from which two substantially parallel shafts are upstanding. Each of the shafts has a pointed end for insertion into the tissue to be repaired and one or more barbs along the length thereof to lock the shaft into the tissue being repaired. The suture is positioned and inserted by pushing the suture through a hollow sleeve with a rigid pusher.

DETAILED DESCRIPTION OF PREFERRED EMBODIMENTS

Figure 1:
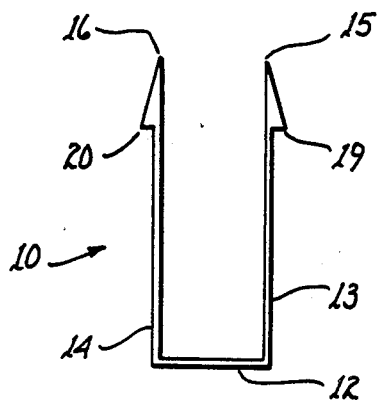
FIGS. 1 and 2 illustrate, in front view, embodiments of surgical sutures.
Figure 2:
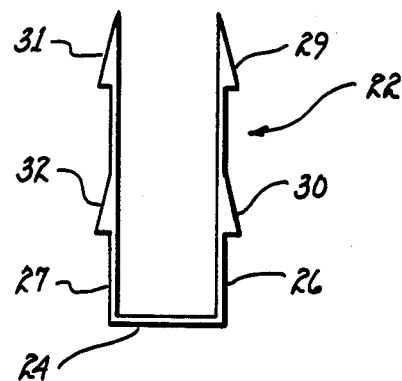

FIGS. 1 and 2 illustrate two embodiments of sutures in accordance with the invention. FIG. 1 illustrates a suture 10 having a base member 12 with two shafts 13, 14 upstanding therefrom. Each of the shafts terminate in a pointed end 15, 16. The pointed ends facilitate the insertion of the suture into the body tissue to be repaired. Barbs 19 and 20 lock the shafts into position in the tissue after insertion. In use, the shafts are inserted into the tissue and across the tear to pull the sides of the tear together, with the barbs maintaining the suture shafts in place.

FIG. 2 illustrates a further embodiment of the invention. Suture 22 includes a base member 24 with substantially parallel shafts 26, 27 upstanding from the opposite ends of the base member. Suture 22 includes two barbs 29, 30 and 31, 32 projecting outwardly from the shafts 26, 27, respectively. Barbs 29 and 31 additionally provide pointed ends to shafts 26, 27 to facilitate insertion of the shafts into body tissue.

The sutures illustrated in FIGS. 1 and 2 are but two illustrations of sutures in accordance with the invention. In general, the sutures include a base member from which a plurality of substantially parallel shafts are upstanding. In a preferred embodiment, the sutures includes two shafts. The plurality of shafts, as contrasted with only a single suture shaft, provide a substantially increased joining strength for holding the opposing edges of a wound together. The insertion of a single multishafted suture replaces the insertion of a plurality of single shaft sutures. In some instances it is difficult, time consuming and even traumatic to individually insert a plurality of sutures.

Sutures in accordance with the invention preferably have a base width of about 3-6 mm in 1 mm increments. Further, the sutures are preferably available having a base thickness of about 1-4 mm, in 1 mm increments. Additionally, sutures in accordance with the invention preferably have a shaft length of about 8-16 mm in 1 mm increments.

The sutures can formed of metal, plastic, biologically absorbable material such as surgical gut, or the like. The base member and upstanding shafts can be of either circular or flat rectangular cross section. The barbs, having a width somewhat greater than the width of the shaft, can be conical, flat triangular projections, or the like. Although only sutures having 1 or 2 barbs on each shaft have been shown, the sutures can, in general, have a plurality of projections.

Figure 3:
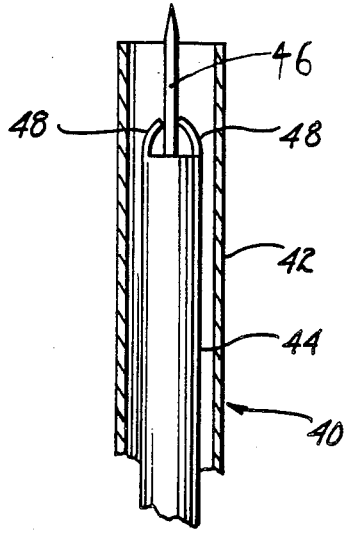
FIGS. 3 and 4 illustrate an insertion sleeve and pusher in vertical and horizontal section, respectively.
Figure 4:
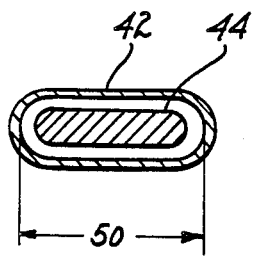

FIGS. 3 and 4 illustrate a delivery system 40 for positioning and inserting sutures in accordance with the invention. Sutures in accordance with the invention are especially designed for the repair of a torn meniscus, for example a knee joint, although such sutures are adaptable for other tissue repair. Use of the suture in such an application, for example in arthroscopic surgery, requires the remote positioning and insertion of the suture. The correct positioning and insertion are facilitated by delivery system 40 in a method as described below. Sutures are provided in a variety of sizes; a delivery system is provided for each size of suture to constitute a surgical suture system.

FIG. 3 illustrates the delivery system in a vertical section. The delivery system includes a hollow tubular sleeve 42 which can be inserted through an incision to the interior of the knee. The sleeve is substantially rigid, and can be either straight or have a variety of angular bends as needed for a particular patient. A pusher rod 44, sized to pass through the hollow interior of the sleeve pushes the surgical suture 46 into the body tissue. The pusher rod preferably is provided with means for releaseably holding the suture until it is properly inserted. The holding means can comprise, for example, a pair of spring clips 48, vacuum means (not shown), or the like. The pusher rod is substantially rigid, having sufficient flexibility to traverse any angular bends in sleeve 42.

FIG. 4 illustrates sleeve 42 and pusher rod 44 in cross section. The sleeve has an elongted cross sectional shape, with the length 50 adapted to receive a suture of particular base width. The pusher rod also has an elongated shape matching the shape of the sleeve. The elongated shape prevents the rotation within the sleeve of the multiple shafted suture and thereby enhances the accuracy of positioning the suture.

Figure 5:
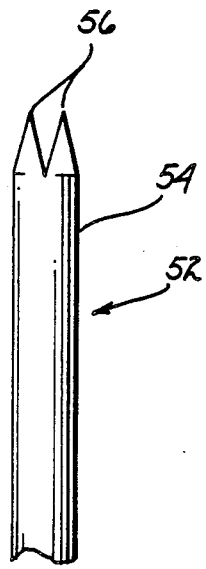
FIG. 5 illustrates a starter.

FIG. 5 illustrates, in side view, a starter 52 which may be used with the sleeve 42 to initiate openings in the body tissue into which the suture is inserted. The starter includes a substantially rigid rod 54 having a plurality of sharp points 56 at the end. The sharp points match the number and position of shafts on the suture being used. The starter is pushed through the sleeve to initiate openings in the tissue into which the suture is inserted. The use of a starter is particularly advantageous when using sutures of a semi-rigid material which would otherwise be difficult to insert into some, especially resistant, body tissue.

Figure 6:
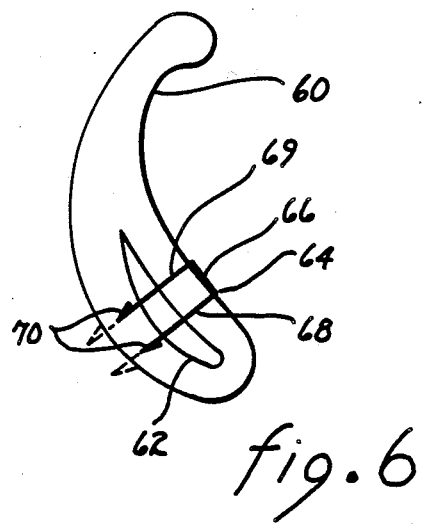
FIG. 6 illustrates a suture in position across a tear in a meniscus.

FIG. 6 illustrates the use and positioning of a suture, in accordance with the invention, in the repair of a torn meniscus 60. Meniscus 60 is shown having a tear 62. Dual shafted suture 64 is inserted into the meniscus tissue so that base member 66 is seated against the surface of the meniscus and shafts 68, 69 pass through the tissue and across tear 62. When fully inserted, the suture pulls the edges of tear 62 together and maintains them in that position while healing occurs. Barbs 70 lock the suture in place. In an alternate embodiment, the shafts may pass completely through the meniscus, as indicated by the dotted lines, with one or more barbs resting on the exterior surface of the meniscus.

Thus it is apparent that there has been provided, in accordance with the invention, a surgical suture and system which fully meet the objects and advantages set forth above. Although the invention has been described with reference to specific embodiments thereof, it is not intended that the invention be limited to those illustrative embodiments. Rather, it is intended that all variations and modifications as fall within the spirit of the invention be included within the appended claims.

I claim:

1. A surgical suturing system comprising:
    a surgical suture having a base member, two substantially parallel shafts upstanding from said base member and having pointed barbs at the ends thereof;
    means for positioning and inserting said suture into body tissue; said means for positioning and inserting comprises:
        a hollow sleeve member through which said suture can be delivered;
        a pusher member sized to fit through the hollow interior of said sleeve member and capable of pushing said suture into said body tissue; and
        a starter member sized to fit through said sleeve member and comprising a substantially rigid rod having two pointed projections at the end thereof, said projections capable of creating two starter holes in said body tissue into which can be inserted said substantially parallel shafts.

2. The suturing system of claim 1 wherein said hollow interior of said hollow sleeve member has an elongate cross section having a long dimension to accomodate the width of said base member of said suture.

3. The suturing system of claim 2 wherein said pusher member has an elongate cross section.

4. The suturing system of claim 1 wherein said pusher member further comprises releaseable means for securing said suture to the end thereof.

* * * * *